United States Patent
Weinzweig et al.

(10) Patent No.: US 11,793,946 B2
(45) Date of Patent: Oct. 24, 2023

(54) DELIVERY DEVICE AND METHOD FOR INTRANASAL ADMINISTRATION OF TOPICAL THERAPEUTIC AGENTS

(71) Applicant: Novaplast Corporation, Boston, MA (US)

(72) Inventors: Jeffrey Weinzweig, Highland Park, IL (US); Ashley Weinzweig, Highland Park, IL (US)

(73) Assignee: Novaplast Corporation, Summerland Key, FL (US)

( * ) Notice: Subject to any disclaimer, the term of this patent is extended or adjusted under 35 U.S.C. 154(b) by 2110 days.

(21) Appl. No.: 15/099,221

(22) Filed: Apr. 14, 2016

(65) Prior Publication Data
US 2017/0296759 A1    Oct. 19, 2017

(51) Int. Cl.
| | |
|---|---|
| *A61M 11/00* | (2006.01) |
| *A61M 31/00* | (2006.01) |
| *A61M 13/00* | (2006.01) |
| *A61M 15/00* | (2006.01) |
| A61M 15/08 | (2006.01) |
| A61M 16/04 | (2006.01) |

(52) U.S. Cl.
CPC .......... *A61M 11/006* (2014.02); *A61M 13/00* (2013.01); *A61M 15/009* (2013.01); *A61M 31/00* (2013.01); *A61M 15/085* (2014.02); *A61M 16/0461* (2013.01); *A61M 2202/0007* (2013.01); *A61M 2202/048* (2013.01); *A61M 2210/0618* (2013.01)

(58) Field of Classification Search
CPC ....... A61M 11/00; A61M 11/06; A61M 13/00
See application file for complete search history.

(56) References Cited

U.S. PATENT DOCUMENTS

| 4,886,493 A | * | 12/1989 | Yee | A61M 11/00 |
| | | | | 604/516 |
| 10,076,441 B2 | * | 9/2018 | Rozenberg | A61M 3/025 |
| 2016/0199599 A1 | * | 7/2016 | Isaacs | A61M 15/08 |
| | | | | 128/200.14 |

(Continued)

OTHER PUBLICATIONS

See "proximate," definition 2.a. ("very near: close"), Merriam-Webster.com Dictionary, Merriam-Webster, https://www.merriam-webster.com/dictionary/proximate. Accessed Nov. 24, 2020; see also id. ("Medical Definition of proximate," definition 1.a. ("very near").*

*Primary Examiner* — LaToya M Louis
(74) *Attorney, Agent, or Firm* — Saul Ewing LLP

(57) ABSTRACT

The present invention provides a delivery device for intranasal administration of topical therapeutic agents to a desired site within a nasal cavity. The delivery device, in some embodiments, comprises a housing defining an interior and adapted to contain a supply of at least one therapeutic agent. The delivery device further includes a flexible connector, which is in fluid communication with the supply in the housing. A distributor, which is also integrally formed with the connector, is also provided. The distributor includes a proximal end that is in fluid communication with a distal end of the connector, and is adapted to receive the supply of the at least one therapeutic agent delivered by way of a conduit. The distributor further includes a distal end defining an outlet configured to diffuse the therapeutic agent when delivered to the treatment site.

10 Claims, 4 Drawing Sheets

(56) References Cited

U.S. PATENT DOCUMENTS

2016/0235786 A1* 8/2016 Hughes ................ A61K 31/714
2016/0361507 A1* 12/2016 Levin ................... A61M 11/006
2016/0367771 A1* 12/2016 Djupesland ....... A61M 15/0021
2017/0157369 A1* 6/2017 Faith ................. A61M 25/1009

* cited by examiner

DELIVERY DEVICE AND METHOD FOR INTRANASAL ADMINISTRATION OF TOPICAL THERAPEUTIC AGENTS

FIELD OF THE INVENTION

This invention relates to a device and method for delivering a topical therapeutic agent in a nasal passage. It is particularly directed to medical devices and methods for delivery of diffused and predetermined amounts of therapeutic agents at a particular location in a nasal passage.

BACKGROUND

Migraines are a common type of headache that the American Headache Society (AHS) estimates to be suffered by approximately 28 million Americans aged 12 years and older. Migraine symptoms include a pounding headache, nausea, vomiting, and light sensitivity. These symptoms are traditionally treated with antinausea drugs and abortive or preventive medications. Headache remedies include pain relievers. A recent procedure that attempts to alleviate pain delivers an anesthetic, such as lidocaine, directly to nerves in the back of the nasal cavity to a nerve center known as the sphenopalatine ganglion.

A device that has been used for such a procedure includes a conventional syringe, an atomizer, and a connector. The connector is disclosed in U.S. Pat. No. 6,112,743. A shortcoming with such a system is that it is not suitable for home use for a number of reasons. First, the amount of therapeutic agent that is to be delivered to a site would need to be measured and carefully delivered by the user. Next, the rate of delivery of the therapeutic agent requires training and experience. Lastly, proper positioning of the atomizer at a treatment site is not within the knowledge of home users.

The present invention provides a device and method that overcomes such shortcomings. Other objects and advantages of the present invention will be made more apparent hereinafter.

SUMMARY OF THE INVENTION

The present invention provides a delivery device for intranasal administration of topical therapeutic agents to a desired site within a nasal cavity. For example, an anesthetic agent may be delivered with a device in accordance with the present invention to the sphenopalatine ganglion to produce desensitization thereof for the treatment of migraine headaches. The delivery device, in some embodiments, comprises a housing defining an interior and adapted to contain a supply of at least one therapeutic agent. In some embodiments, the housing may be fully enclosed with the supply contained therein. In other embodiments, the housing may include a closable opening into which a pre-measured supply of therapeutic agent may be received. The delivery device further includes a flexible connector. The connector is integrally formed with the housing and defines conduit and a proximal end, which is in fluid communication with the supply in the housing. In some embodiments the connector may be malleable such that it may be bent into a desired form that maintains its shape. In other embodiments, the connector may be relatively pliable and malleable such that no specific shape is maintained. A distributor, which is also integrally formed with the connector, is provided. The distributor includes a proximal end that is in fluid communication with a distal end of the connector, and is adapted to receive the supply of the at least one therapeutic agent delivered by way of the conduit. The distributor further includes a distal end defining an outlet. The outlet is configured to diffuse the at least one therapeutic agent when delivered to the treatment site. Operatively connected to the supply in the housing is an actuator that causes the supply of the at least one therapeutic agent to be released from the housing through the conduit, through the distributor, and out of the outlet. In some embodiments, an indicator is provided on the connector. The indicator will provide the user with a guide so the user is able to determine how far to insert the distributor into the nasal cavity. This indicator my include markings. In a preferred embodiment, the indicator may comprise a hub adapted to contact the nostril when at the desired position.

One possible use for the present invention is to deliver a topical anesthetic agent, such as 0.5% Marcaine, to the sphenopalatine ganglion, i.e., SPG blocks, to produce desensitization of the ganglion for the treatment of migraine headaches. Another use for the present invention is to delivery topical anti-inflammatory and decongestant agents, such as Oxymetazoline, for the treatment of nasal congestion and sinusitis. The present invention may also be used to delivery variety of topical steroid agents, such as triamcinolone acetonide, for the treatment of seasonal allergies and hay fever.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

There is shown in the drawing presently preferred embodiments of the present invention.

Figure 1:
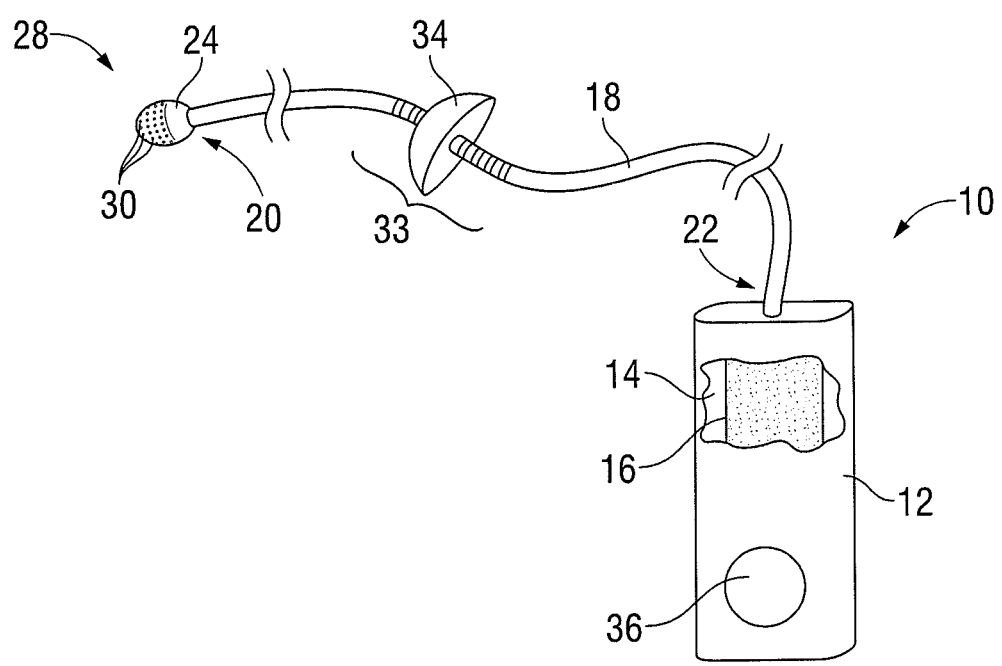
FIG. 1 is perspective view of a preferred embodiment of the present invention for a single use application.

It should be noted that the drawings of the invention are not to scale. The drawings are merely schematic representations, not intended to portray specific parameters of the invention. The drawings are intended to depict only typical embodiments of the invention, and therefore should not be considered as limiting the scope of the invention. The invention will be described with additional specificity and detail through the use of the accompanying drawings. In the drawings like numbering represents like elements between the drawings.

DETAILED DESCRIPTION OF THE PREFERRED EMBODIMENTS

There is shown in FIG. 1 of the drawings, a preferred embodiment of the present invention. The delivery device 10 comprises a housing 12, which defines an interior 14. The interior 14 is adapted to contain a supply 16 of at least one therapeutic agent. The supply 16 may be a liquid agent contained solely by the interior 14. Alternatively, the supply may be an encapsulated aliquot of the therapeutic agent, discussed below. In the present embodiment, the housing is fully enclosed with the supply contained therein. The housing may be filled with a desired amount of the agent and then sealed. As such, there is no need for the user to measure the therapeutic agent to be delivered since the device is self-contained and ready-for-use.

A flexible connector 18 is provided. The connector 18 defines a distal end 20 and a proximal end 22. The connector further defines an internal conduit through which the therapeutic agent may pass. The proximal end 22 of the connector is in fluid communication with the housing 12, and more particularly, the supply 16 in the interior 14 of the housing. In order to maintain a sterile environment, the connector 18 is integrally formed with the housing 12. By providing a self-contained unit, and not requiring a user to connect various parts of the device, the risk of introduction of contaminants is reduced or eliminated. The connector is preferably of a malleable material that enables it to be bent into a desired shape for use, as will be discussed in greater detail below. Use of a malleable material, while not required, allows for greater ease of use. This hub may provide the user with tactile feedback The proximal end 22 of the connector 18 is connected, and preferably integrally formed with, and in fluid communication with a proximal end 26 of a distributor 24. The distal end 28 of the distributor defines an outlet 30. The outlet 30 is configured to diffuse, and preferably atomize, the supply 16 of therapeutic agent as it is urged out of the outlet 30.

In some embodiments, the connector 18 may include an indicator such as markings 33, and may further include a hub 34. The indicator provides the user with an indication to allow proper positioning of the distributor 24 within the nasal cavity. For example, when used to deliver a topical anesthetic agent, such as 0.5% Marcaine, to the sphenopalatine ganglion, so as to provide relief from migraine headaches, the indicator, such as hub 34, will be positioned on the connector 18, such that when the hub contacts the user's nostril (FIG. 2), the outlet 30 will be positioned approximately 3.5 to 4 cm from the nasal sill so the anesthetic is delivered to the sphenopalatine ganglion. When delivering other types of therapeutic agents where the desired location of delivery is a different distance from the nasal sill, the hub 34 would be positioned to accommodate such a delivery site. In so doing, the user need not make any decisions regarding proper delivery of the therapeutic agent.

Figure 2:
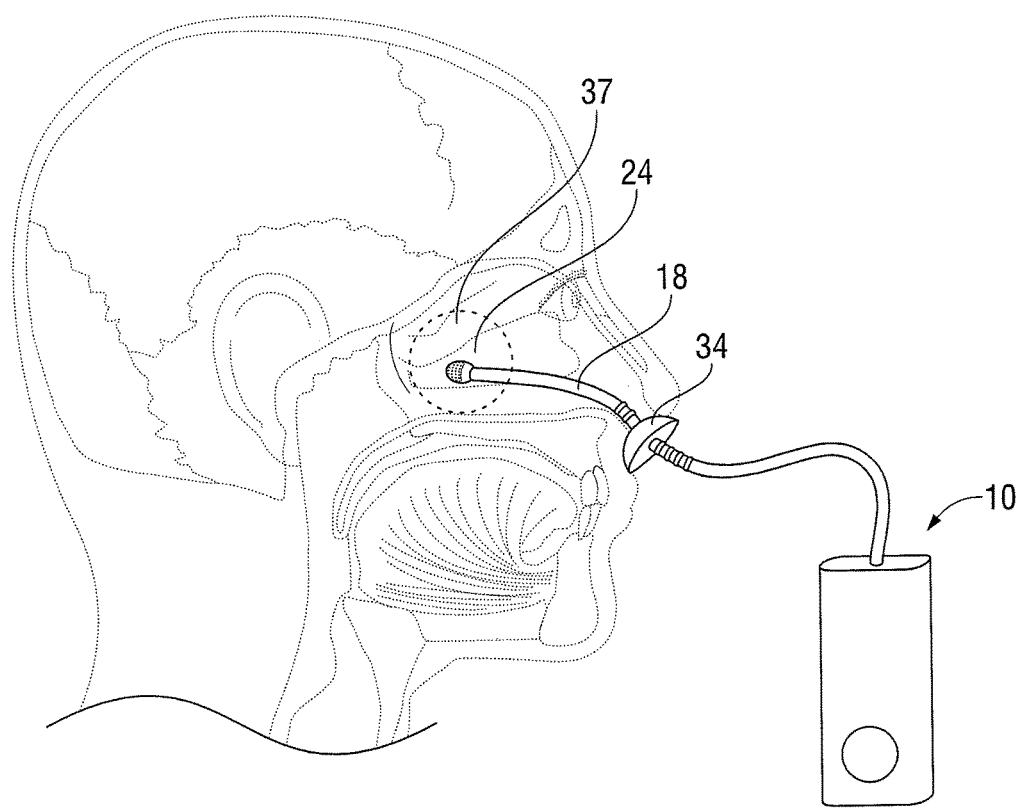
FIG. 2 is a schematic view of the preferred embodiment of FIG. 1 with the device in position for delivery of the therapeutic agent.

Shown schematically in FIGS. 1 and 2 is an actuator 36. The actuator 36 is operatively connected to the supply 16 in the housing 12 so that activation of the actuator will cause the supply to be transmitted from the housing 12, through the connector 18, through the distributor 24 and its outlet 30. A variety of actuators may be utilized for this purpose, as will be understood by those skilled in the art. The actuator, utilizing a spring mechanism, would, when activated by depression of a button release mechanism, cause the contents of the supply chamber to be forced through the connector toward and through the distal atomizer for delivery at the target site.

Referring to FIG. 2, a method of using the embodiment of FIG. 1 is explained. A user will insert the distributor 24 into the nasal passage. In a preferred embodiment, the distributor may include a lubricant to make insertion easier. The distributor 24 and connector 18 are guided up into the nasal cavity until the hub 34 contacts the nasal sill. The user then activates the actuator 36 so that the supply 16 is urged through device 10 out of outlet 30 to the desired treatment site 37. In this single-use embodiment, the device is then discarded.

In one example, delivery of 0.5% Marcaine to the sphenopalatine ganglion (SPG) for the purpose of desensitizing the SPG for the management of migraine headaches, the shield would be positioned at 3.5-4 cm from the atomizer to allow the atomizer to be advanced that distance within the nasal passage where the SPG is anatomically located. The arc of the connector would be curved approximately 45 degrees prior to insertion into the nasal passage and the atomizer distal end would be directed toward the ear on the same side. Such positioning would maximize the delivery of the agent to the SPG. Once sufficiently positioned, the activator button on the medication chamber is depressed and the treatment agent is released and transferred from the chamber, down the connector, and through the atomizer to reach its preferred target. Such a simple and effective mechanism can be performed by either a health care provider or as a home use device for self-administration by a patient. The predetermined aliquot of 0.5% Marcaine contained within the chamber ensures delivery of the proper dosage of the therapeutic agent.

Figure 3A:
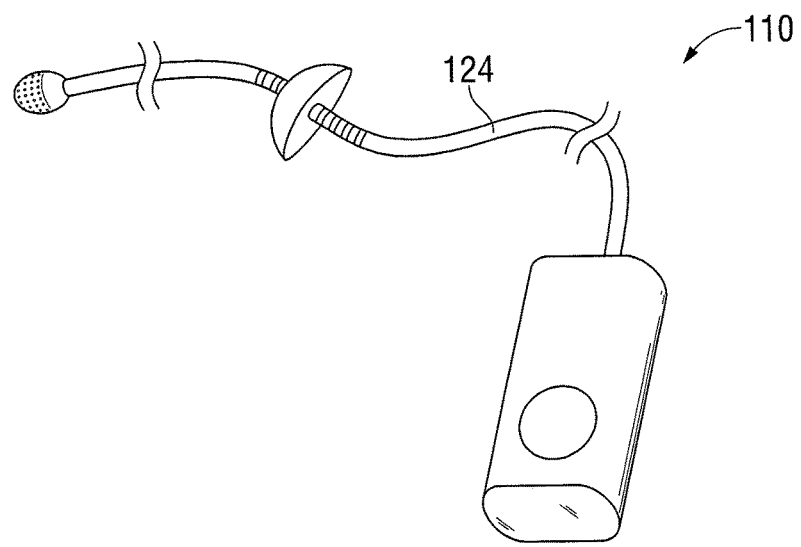
FIG. 3A is a perspective view of an alternative preferred embodiment of the present invention that is suitable for multiple use applications.
Figure 3B:
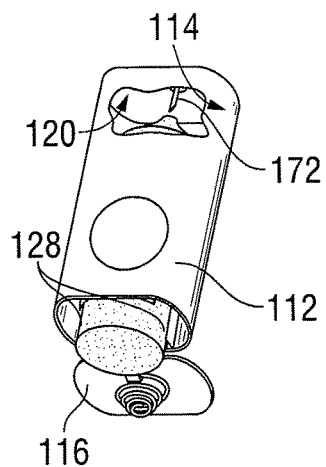
FIG. 3B is a partial view of the housing of the embodiment of FIG. 3A with a cutaway portion to view a portion of the interior.
Figure 3C:
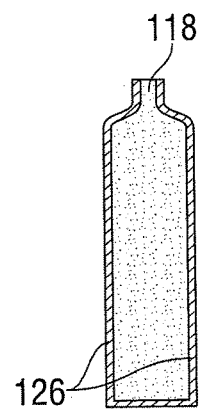
FIG. 3C is a cross sectional view of a supply of therapeutic agent.

While the previous embodiment depicted a single-use device, in other embodiments, the device may be reloaded. Referring to FIGS. 3A-3C, a multi-use device 110 is shown. In many respects, this embodiment is similar to the previous embodiment. A difference, however, is that the interior 114 of the housing 112 may be accessed by the user by way of a closeable opening, such as lid 116. Sealed supplies, such as supply 118 may be inserted by the user into the housing 112. In this embodiment, the interior 114 of the housing 112, may include, at its distal end 120, a piercing structure 122 that is adapted to puncture the supply 118 so the therapeutic agent therein is connected to the connector 124. In a preferred embodiment, the piercing structure 122 is configured to both pierce the supply 118, while also creating a seal with the exterior of the supply so prevent loss of the therapeutic agent. In order to make the insertion of the supply even more user friendly, the supply 118 may include one or more slots 126 that are guided into cooperating guides 128 formed with the interior 114 of the housing 112 so the supply 118 is properly aligned. In a preferred embodiment, the closing of the lid 116 will cause the supply 118 to be urged against the piercing structure with sufficient force to connect the connector 124 to the therapeutic agent. Once the closeable opening is re-closed, device 110 is operated in the same manner as previously discussed.

Figure 4A:
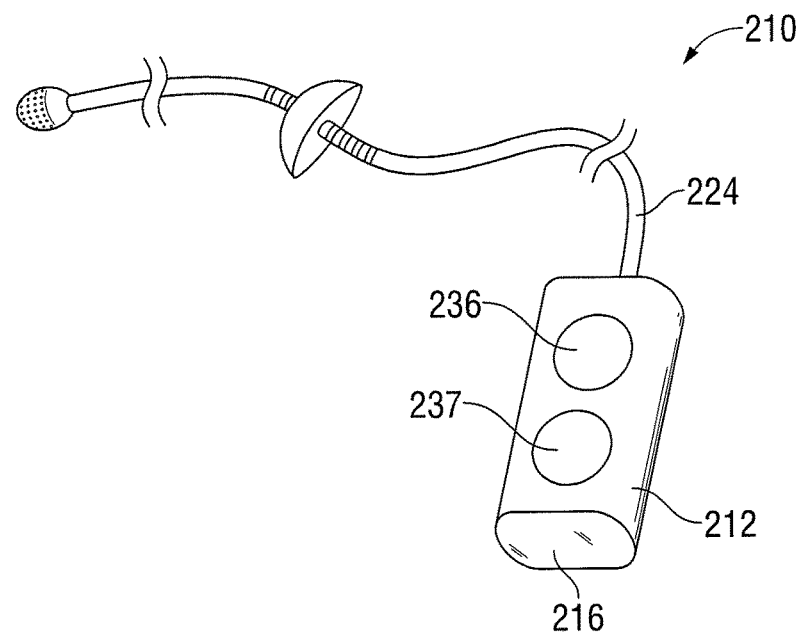
FIG. 4A is a perspective view of an alternative preferred embodiment of the present invention that is suitable for multiple use applications.
Figure 4B:
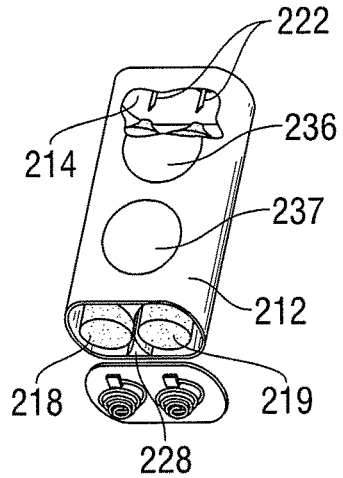
FIG. 4B is a partial view of the housing of the embodiment of FIG. 3A with a cutaway portion to view a portion of the interior.

Yet another version of a multi-use embodiment is shown discussed in conjunction with FIGS. 4A-4B. In this embodiment, a multi-use device 210 is shown. In many respects, this embodiment is similar to FIGS. 3A-3C. Similar to FIGS. 3A-3C, the interior 214 of the housing 212 may be accessed by the user by way of a closeable opening, such as lid 216. Sealed supplies, such as supply 218 and supply 219 may be inserted by the user into the housing 212. In this embodiment, the interior 214 of the housing 212, may include, at its distal end 220, a pair of piercing structures 222, which are adapted to puncture each of supply 218 and 219 so the therapeutic agent in each supply is connected to the connector 224. The supplies 218 and 219 may be guided by cooperating guide 228 formed with the interior 214 of the housing 212 so each of supplies 218 and 219 is properly aligned. In a preferred embodiment, the closing of the lid 216 will cause supply 218 and 219 to be urged against the piercing structure with sufficient force to connect the connector 224 to the therapeutic agent. Such an embodiment is particularly useful where a therapeutic agent is to be delivered in separate nasal passages. The housing 212, in this embodiment, includes two separate actuators 236 and 237, which are shown schematically. It should be understood that a single actuator may be used to actuate delivery of each supply. In this preferred embodiment, the supplies are loaded by the device supplier, and the lid, when closed, is not re-openable without damaging the housing. This minimizes the possibility of tampering of the therapeutic agent, as well as greater control over the supplies loaded into the device. In this embodiment, the device 210 would allow for a separate delivery of therapeutic agent in separate nasal passages to complete a single treatment cycle with a single device.

In some situations, however, it may be desired that the supplies 218 and 219 may be reloaded. In such a circumstance, the lid 216 would include a latching mechanism, not shown, which would allow it to be selectably opened and closed.

While a presently preferred embodiment of the present invention has been shown and described, it will be apparent that modifications may be made without departing from the scope of the invention as defined in the attached claims.

What is claimed is:

1. A delivery device for intranasal administration of topical therapeutic agents, the delivery device comprising:
    a housing adapted to contain a supply of at least one therapeutic agent;
    a flexible connector integrally formed with the housing and defining a conduit, the connector further comprising a connector proximal end in fluid communication with the housing and a connector distal end;
    a distributor integrally formed with the connector about the connector distal end, the distributor including a distributor proximal end adapted to receive the supply of the at least one therapeutic agent delivered by way of the conduit, the distributor further including a distributor distal end adapted to diffuse the at least one therapeutic agent to a treatment site as a fine mist, the flexible connector further including an adjustable indicator configured to position the distributor distal end about 3.5 cm to 4 cm from the indicator; and
    an actuator adapted to cause the supply of the at least one therapeutic agent to proceed from the housing through the conduit, and exit the distributor.

2. The delivery device of claim 1, the housing including closable access portion adapted to receive a second supply of the at least one therapeutic agent.

3. The delivery device of claim 1, wherein the indicator comprises hub member.

4. The delivery device of claim 1, the housing adapted to contain a plurality of supplies of therapeutic agent, and each supply of therapeutic agent is selectively actuated for delivery.

5. The delivery device of claim 4, wherein the housing includes a closable access portion adapted to receive at least one additional supply of the at least one therapeutic agent.

6. A delivery device for intranasal administration of a topical therapeutic agent, the delivery device comprising:
    a housing including a predetermined supply of at least one therapeutic agent;
    a flexible connector having a connector proximal end and a connector distal end, the connector proximal end in fluid communication with the housing and supply therein;
    a distributor in fluid communication with the connector distal end, the distributor defining an outlet adapted to diffuse the therapeutic agent as a fine mist, the flexible connector further including an adjustable indicator configured to selectively position the distributor distal end about 3.5 to 4 cm from the indicator; and
    an actuator adapted to cause the supply to pass from the housing through the connector to the distributor and through the outlet.

7. The delivery device of claim 1, wherein the indicator comprises hub member.

8. The delivery device of claim 6, the housing including closable access portion adapted to receive a second supply of the at least one therapeutic agent.

9. The delivery device of claim 6, the housing adapted to contain a plurality of supplies of therapeutic agent, and each supply of therapeutic agent is selectively actuated for delivery.

10. The delivery device of claim 9, wherein the housing includes a closable access portion adapted to receive at least one additional supply of the at least one therapeutic agent.

* * * * *